US006627448B1

(12) United States Patent
Lawlor et al.

(10) Patent No.: US 6,627,448 B1
(45) Date of Patent: Sep. 30, 2003

(54) ANALYTE-BINDING ASSAY

(75) Inventors: Joseph F. Lawlor, Arlington, MA (US);
Gordon C. Siek, Somerville, MA (US);
Joseph D. Musto, Dover, MA (US)

(73) Assignee: Reference Diagnostics, Inc., Bedford, MA (US)

(*) Notice: Subject to any disclaimer, the term of this patent is extended or adjusted under 35 U.S.C. 154(b) by 193 days.

(21) Appl. No.: 09/678,462

(22) Filed: Oct. 3, 2000

Related U.S. Application Data

(60) Provisional application No. 60/157,551, filed on Oct. 4, 1999.

(51) Int. Cl.[7] ............................................. G01N 33/20
(52) U.S. Cl. ............................ 436/74; 422/61; 436/73; 436/84; 436/166
(58) Field of Search ....................... 436/73, 74, 84, 436/166, 183; 422/61

(56) References Cited

U.S. PATENT DOCUMENTS

| | | | |
|---|---|---|---|
| 3,537,822 A | * 11/1970 | O'Malley et al. ............. 436/74 |
| 3,887,332 A | * 6/1975 | Takase et al. | |
| 3,925,020 A | 12/1975 | Ogawa et al. | |
| 4,224,034 A | 9/1980 | Denney et al. | |
| 4,308,027 A | 12/1981 | Ceriotti | |
| 4,407,962 A | * 10/1983 | Tabacco et al. ............... 436/74 |
| 4,588,695 A | 5/1986 | Takano et al. | |
| 4,703,015 A | * 10/1987 | Tabacco et al. ............... 436/74 |
| 4,810,656 A | * 3/1989 | Torelli ........................... 436/74 |
| 5,104,865 A | 4/1992 | Hider et al. | |
| 5,151,370 A | * 9/1992 | Denney ......................... 436/74 |
| 5,186,894 A | 2/1993 | Katsuyama | |
| 5,922,761 A | 7/1999 | Lai | |

FOREIGN PATENT DOCUMENTS

| EP | 61793 | * 10/1982 | |
|---|---|---|---|
| JP | 58-144750 | * 8/1983 | |

OTHER PUBLICATIONS

Truhaht, R. et al, Ann. Biol. Clin. 1959, 17, 571–587.*
Beale, R. N. et al, J. Clin. Path. 1961, 14, 488–495.*
Beale, R. N. et al, J. Clin. Path. 1962, 15, 156–160.*
Altounian A. Canadian Journal of Medical Technology 1978, 40, D36–D38, D40–D42.*
Paris, M. et al, Ann. Biol. Clin. 1986, 44, 511–516.*
Brivio, G. et al, La Ricerca Clin. Lab. 1986, 16, 523–532.*
J. C. Houston et al, Guy's Hosp. Repts. 1953, 102, 355–359.*
B. Zak et al, Clinical Chemistry 1965, 11, 641–644.*
J. A. O'Malley et al, Clinical Chemistry 1970, 16, 92–96.*
R. G. Martinek J. Am. Med. Technol. 1970, 32, 582–589.*
J. L. A. Hunteler et al, Clinica Chimica Acta 1972, 37, 391–397.*
R. Haeckel Zeitschrift fuer Klinische Chemie und Klinische Biochemie 1973, 11, 301–307.*
A. Kyaw Clinica Chimica Acta 1976, 69, 351–354.*
R. T. Card et al, Chem. Abstr. 1964, 60, abstract 12353a.*
H. L. Williams et al, J. Lab. Clin. Med. 1966, 67, 171–176.*
J. F. Goodwin Clin. Biochem. 1970, 3, 307–314.*
P. Leflon et al, Ann. Biol. Clin. 1975, 33, 97–103.*
F. Watanabe et al, Japan J. Clin. Chem. 1975, 3, 460–463.*
J. Burnichon et al, Chem. Abstr. 1975, 82, abstract 151659r.*
A Garcic Clin. Chim. Acta 1979, 94, 115–119.*
D. Gotzmannova et al, Collect. Czech. Chem. Commun. 1980, 45, 1793–1804.*
A. Tabacco et al, Clin. Chim. Acta 1981, 114, 287–290.*
H. Yamanishi et al, Clin. Chem. 1997, 43, 2413–2417.*

* cited by examiner

*Primary Examiner*—Arlen Soderquist
(74) *Attorney, Agent, or Firm*—Fish & Richardson P.C.

(57) ABSTRACT

Analyte-binding assays, such as iron binding assays, are disclosed. The assays can provide information relating to the serum iron content and/or total iron binding capacity of a sample.

21 Claims, 2 Drawing Sheets

ANALYTE-BINDING ASSAY

CROSS-REFERENCE TO RELATED APPLICATION

This application claims priority under 35 U.S.C. §119 to U.S. Provisional Patent Application Serial No. 60/157,551, filed on Oct. 4, 1999, and entitled "Iron Binding Assay," the entire contents of which are hereby incorporated by reference.

TECHNICAL FIELD

The invention relates to analyte-binding assays, such as iron binding assays.

BACKGROUND

Serum total iron binding capacity (TIBC) can be used to assess a patient's iron metabolic state. Typically, at least about 95% of iron in serum is bound by transferrin that binds ferric iron with an anion (preferably bicarbonate) at pH greater than about 5. Often, only about ⅓ of the transferrin serum binding sites are occupied with iron.

SUMMARY

The invention relates to analyte-binding assays, such as iron binding assays.

In one aspect, the invention generally features a method of evaluating a sample. The sample includes an analyte-binding compound and an analyte capable of binding to the analyte-binding compound to form an analyte-compound complex. The method includes combining the sample with an analyte-binding dye to form a first mixture. The analyte-binding dye is capable of binding to the analyte to form an analyte-dye complex. The method also includes comparing a measurement of the amount of the analyte-dye complex in the first mixture taken under a first condition to a measurement of the amount of the analyte-dye complex in a second mixture that includes the first mixture taken under a different condition. The affinity of the analyte-binding compound for the analyte under the first condition is different from the affinity of the analyte-binding compound under the second condition (e.g., the affinity of the analyte-binding compound for the analyte under the first condition is less than the affinity of the analyte-binding compound for the analyte under the second condition).

The measurements can be made by evaluating the ability of the analyte-dye complex to interact with energy (e.g., by measuring absorbance, emission and/or reflectivity).

The first condition can be one pH and the second condition can be a different pH. For example, the first pH can be lower than the second pH.

The analyte can be iron ions (e.g., ferric ions), the analyte-binding dye can be an iron-binding dye, and the analyte-binding compound can be transferrin.

The method can take less than about 45 minutes.

The method can include adding a base to the first mixture to form the second mixture.

In some embodiments, less than about 5% of the analyte in the first mixture is bound to the analyte-binding compound in the first mixture under the first condition.

The first mixture can include sufficient analyte so that substantially all the analyte-binding compound is saturated with the analyte in the second mixture, and the method can be performed without further addition of analyte.

The difference between the first and second measurements can be proportional to the total iron binding capacity of the sample.

In another aspect, the invention generally features a method of evaluating a sample containing ferric ions and transferrin. The method includes combining the sample with an iron-binding dye to form a first mixture. The iron-binding dye is capable of binding ferric ions to form an iron-dye complex. The method also includes comparing a measurement of the amount of the iron-dye complex in the first mixture to a measurement of the amount of the iron-dye complex in a second mixture that includes the first mixture. The first measurement is made at one pH (e.g., less than about 5.7) and the second measurement is made at a higher pH (e.g., greater than about 5.7).

The iron-binding dye can be a fluorescent dye and/or a colorimetric dye. For example, the iron-binding dye can be Eriochromcyanine R, Chromazurol S and/or Chromazurol B.

The first mixture can contain excess ferric ions and/or excess iron-binding dye.

In some embodiments, less than about 5% of the ferric ions in the first mixture are bound to transferrin at the first pH.

The first mixture can contain a sufficient amount of ferric ions so that substantially all the transferrin is saturated with ferric ions in the second mixture.

In certain embodiments, the difference between the first and second measurements is proportional to the total iron binding capacity of the sample.

In a further aspect, the invention generally relates to a method of determining the amount of iron in a sample and the total iron binding capacity of the sample. The method includes comparing a measurement of the amount of an iron-dye complex in a first mixture, which contains the sample, to a measurement of the saturating amount of the iron-dye complex in the absence of the sample to determine the amount of iron in the sample. The mixture is measured when under a first condition. The method also includes comparing a measurement of the amount of the iron-dye complex in a second mixture, which contains the first mixture, to the measurement of the iron-dye complex in the first mixture to determine the total iron binding capacity of the sample. The second measurement of iron-dye complex in the second mixture is made when the second mixture is under a second condition that is different from the first condition.

The method can further include combining the sample with a composition to form the first mixture. The composition can contain a sufficient amount of the iron and/or iron-dye complex so that first mixture contains the saturating amount of iron and/or the iron-dye complex.

The sample can contain ferric ions and transferrin.

The first condition can be one pH, and the second condition can be a different pH. For example, the first condition can be a lower pH than the second condition.

The method can include adding a base to the first mixture to form the second mixture.

The first mixture can contain a sufficient amount ferric ions so that substantially all the transferrin contained in the second mixture is saturated with ferric ions.

The sample can be a serum sample.

In another aspect, the invention generally relates to a method of determining the amount of an analyte in a sample and the amount of an analyte-binding compound in the sample. The analyte-binding compound is capable of binding the analyte to form an analyte-compound complex. The method includes comparing a first measurement of the amount of an analyte-dye complex in a first mixture, which contains the sample, to a measurement of the saturating amount of the analyte-dye complex in the absence of the sample to determine the amount of the analyte in the sample. The first measurement is made when the mixture is under a first condition. The method also includes comparing a second measurement of the amount of the analyte-dye complex in a second mixture, which contains the first mixture, to the first measurement of the analyte-dye complex in the first mixture to determine the amount of analyte-binding compound in the sample. The second measurement of analyte-dye complex in the second mixture is made when the second mixture is under a second condition different from the first condition.

In another aspect, the invention includes a reagent discussed herein or a kit including one or more reagent described herein and optionally one or more of calibration standards and instructions.

The assay can provide the advantage of not requiring a separate step in which free iron is isolated from bound iron. This can reduce the time and cost associated with the assay relative to other iron binding assays which involve a separate step in which free iron is isolated from bound iron.

The invention can be advantageous because it can reduce and/or eliminate biases that can exist between commercially available methods of indirectly making TIBC measurements and other conventional methods.

The invention can be advantageous because the assay can reduce sample manipulation and/or allow determination of serum iron and TIBC in a single assay.

The invention can be advantageous because the assay can be conducted under conditions where the saturating iron present in the reagent can be more stable as part of the analyte-dye complex.

One potential advantage of the invention is that the assay can be conducted in a relatively short period of time.

Another potential advantage of the invention is that the assay can be conducted in a single vessel (e.g., without using multiple vessels).

A further potential advantage of the invention is that the assay can be conducted without removing the analyte from the mixture (e.g., without removing the analyte from the mixture under the first condition or under the second condition).

Another potential advantage of the invention is that it can provide methods of measuring the percent analyte saturation (e.g., percent iron saturation) of a sample in a single process (e.g., using one reaction vessel, without removing the analyte from the mixture and/or without isolating the analyte from the mixture).

Other features and advantages of the invention will be apparent from the figures, the following detailed description, and from the claims.

DETAILED DESCRIPTION

Figure 1:
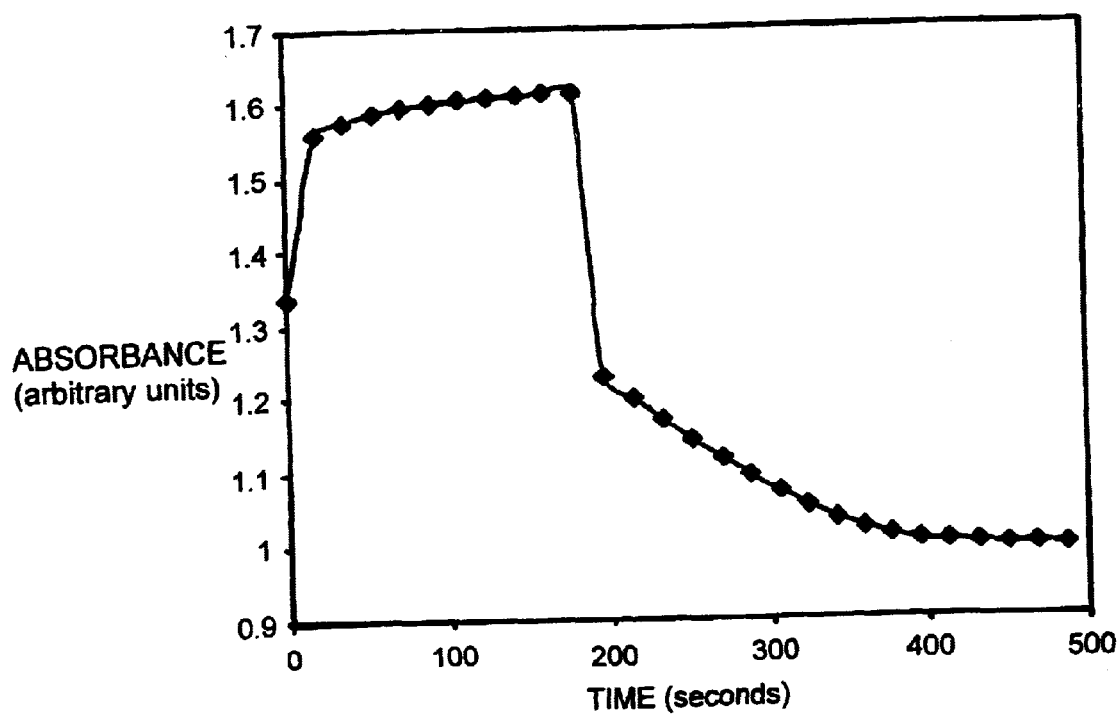
FIG. 1 is a plot of absorbance as a function of time.

The invention relates to analyte-binding assays, such as iron binding assays.

In some embodiments, an iron binding assay includes combining an analyte of interest with an analyte-binding dye that is capable of binding the analyte of interest to form a mixture that contains an analyte-dye complex.

Examples of analytes of interest include iron, such as ferrous ions and/or ferric ions. Typically, the analyte of interest is ferric ions.

Analyte-binding dyes suitable for use in the invention can interact (e.g., bind, complex) with the analyte of interest to form an entity (referred to herein as a complex) in which one or more energy interactive parameters (e.g., absorption, emission and/or reflectivity related parameter(s)) in the complex differ from the corresponding parameter(s) for the analyte-binding dye (uncomplexed dye).

In embodiments in which the analyte of interest is ferric ions, the analyte-binding dye should be capable of interacting with ferric ions to form an iron-dye complex in which, for example, the absorbance, reflectance and/or emission of the iron-dye complex is different from the corresponding parameter(s) for the analyte-binding dye (uncomplexed dye).

In some embodiments, more than one analyte-binding dye can be used.

Examples of analyte-binding dyes include fluorescent dyes and colorometric dyes.

Examples of fluorescent dyes include calcein blue, and flouresceinated desferroxamine, and stibenefloublue-5.

Examples of colorometric dyes include 2,2'-dipyridyl, ortho-phenanthroline, bathophenathroline, 5-Nitro-1,10-phenathroline, methylxylenol blue, xylenol orange, N-benzoyl-N-phenylhyrdroxylamine, N-benzoyl-N-(2-methylphenyl) hydroxylamine, chromotrophic acid, 2-[(5-Bromo-2pyridy10-]5-azo[N-propyl-N-(3-sulfopropyl) amino]aniline, 1,8-dihydroxy-2-(2-pyridylazo)-3,6-napthalenedisulfonic acid, tiron, terosite, 2,4,6-tripyridyl-s-triazine, 2-Nitro-5-[N-n-propyl-N-(3-sulfopropyl)amino] phenol, 2-Nitro-5[N-ethyl-N-(3-sulfopropyl) amino]phenol, 3-(2-pyridyrl)-5,6-bis(4-sulfophenyl)-1,2,4-triazine (ferrozine), ferene, ferrachrome, hydroxamic acids (e.g., phenyl aceto hydroxamic acid), Eriochromcyanine R, Chromazurol S, and Chromazurol B. In certain embodiments, such as when ferric ions are used, the dye(s) include one or more of Eriochromcyanine R, Chromazurol S, and Chromazural B.

The form of energy used in the evaluation(s) can be, for example, light (e.g., IR, visible and/or UV). Evaluation can include, for example, measurement of reflectance, chemiluminescence and/or fluorescence. Evaluation can include taking a spectrum (e.g., a reflectance spectrum, a chemiluminescence spectrum and/or a fluorescence spectrum).

Determination of TIBC

In some embodiments, TIBC is determined as follows.

An analyte-binding dye-containing reagent buffered to a pH of less than about 5.7 (e.g., from about 1 to about 5.7, from about 3 to about 5.2, from about 3.5 to about 5) and iron (generally, excess iron) are added to a serum sample to form a mixture. The dye-containing reagent contains an excess amount of the analyte-binding dye.

The reagent can include any required reagents, such as, for example, surfactant(s) and/or solvent(s), such as cetrimide, N-methyl pyrolidine and/or Tween.

The excess iron is present in the mixture in an amount sufficient to saturate the iron binding sites of the transferrin initially present in the serum sample under conditions that would allow such saturation (e.g., at about neutral pH).

After being combined, the components of the mixture are allowed to react (e.g., by incubating the components). Generally, the components of the mixture are allowed to react for a period of time and under conditions sufficient for the transfer of iron from transferrin to the iron-binding dye to occur. Iron that was initially bound to the transferrin in the serum sample can be released and interact with the dye to form an iron-dye complex, depending upon the affinity of the dye for iron relative to the affinity of transferrin for iron. Under relatively acidic conditions, the affinity of many dyes for iron is higher than the affinity of transferrin for iron.

In certain embodiments, less than about 5% of the iron in the sample is bound to transferrin (e.g., less than about 3% of the iron in the sample is bound to transferrin, less than about 2% of the iron in the sample is bound to transferrin, less than about 1% of the iron in the sample is bound to transferrin, substantially none of the iron in the sample is bound to transferrin) after the components are allowed to react.

After the components of the mixture are reacted, the amount of iron-dye complex is evaluated, for example, by measuring the absorbance, reflectance, chemiluminescence and/or fluorescence of the iron-dye complex. The amount of iron-dye complex corresponds, either directly or indirectly, to the amount of excess iron present in the reagent plus the amount of iron that was in the serum sample.

After evaluating the amount of iron-dye complex present in the mixture, the pH of the mixture is increased to at least about 5.7 (e.g., to at least about 7, from about 5.7 to about 12, from about 7 to 10, from about 7.2 to about 9.5). The pH can be increased, for example, by adding a base, such as a buffered base, to the mixture.

Examples of bases include amine-containing buffers (e.g., Tris, MOPS, MES, Bicine, TAPS CHES, ethanolamine and diethanolamine), a barbital buffer, glycyl-glycine piperazine, clycine, sodium hydroxide, potassium hydroxide, glycine, phosphate, borate, and bicarbonate. In some embodiments, the base is sodium hydroxide, potassium hydroxide, glycine, phosphate, borate or bicarbonate. In certain embodiments, the base is phosphate, borate or bicarbonate. In some embodiments, a combination of MOPS and bicarbonate is used.

In some embodiments, more than one base and/or buffer can be used.

After increasing the pH of the mixture, the components of the mixture are allowed to react (e.g., by incubating the components). Iron that was bound to the dye can be released and bind to the transferrin, depending upon the affinity of transferrin for iron relative to the affinity of the dye for iron. Under relatively basic conditions, the affinity of transferrin for iron is higher than the affinity of many dyes for iron.

After the components of the mixture are reacted, the amount of iron-dye complex is evaluated, for example, by measuring the absorbance, reflectance, chemiluminescence and/or fluorescence of the iron-dye complex. The amount of iron-dye complex corresponds, either directly or indirectly, to the amount of excess iron added to the mixture and the amount of iron that was in the serum sample.

The parameter evaluated at lower pH to measure the iron-dye complex is compared to the parameter evaluated at higher pH to measure the iron-dye complex (e.g., by subtracting the parameter measured at lower pH from the parameter measured at higher pH, or by subtracting the parameter measured at higher pH from the parameter measured at lower pH). A change in the measurement of the iron-dye complex is due to the binding of iron to transferrin. The change in the measurement is proportional to the TIBC.

For example, the absorbance of the mixture at an analyte-dye complex absorption wavelength at the lower pH can be compared to the absorbance of the mixture at an analyte-dye complex absorption wavelength. As will be appreciated by those skilled in the art, the analyte-dye complex absorption wavelengths used at the different pH's can be the same or they can be different. Likewise, combinations of, for example, absorption, reflectance and/or emission data at the different pH's can be compared in conducting the assay.

The absorption, reflectance and/or emission data can be measured using a wavelength of energy at which the parameter measured (e.g., absorption, reflectance and/or emission) of the analyte-dye complex is substantially greater than for the analyte-binding dye (uncomplexed) (e.g., 2 times as much, 10 times as much, 50 times as much, 100 times as much, 500 times as much, 1000 times as much).

In certain embodiments, the assay can be conducted in a relatively short period of time. The assay can be conducted in a relatively short period of time, such as, for example, less than about 45 minutes (e.g., less than about 25 minutes, less than about 20 minutes, less than about 15 minutes, less than about 10 minutes, less than about 5 minutes, less than about 2 minutes).

In some embodiments, the assay can be performed in a single vessel (e.g., without the use of multiple vessels).

In certain embodiments, the assay can be performed without removing iron from the mixture (e.g., without removing iron from the mixture at lower pH or at higher pH).

Determination of Serum Iron and TIBC Follow S

In certain embodiments, both serum iron and TIBC can be evaluated within a single run of the assay. These embodiments can be thought of as including two phases, with the serum iron being determined in the first phase and the TIBC being determined in the second phase.

In the first phase, a composition (e.g., a reagent blank) containing a saturating amount iron and iron-dye complex is evaluated (e.g., by measuring absorbance, reflectance and/or emission). The reagent blank contains an excess of the analyte-binding dye. Serum is added to the reagent blank and allowed to react to form a mixture (e.g., by incubating the components of the mixture). The mixture is evaluated (e.g., by measuring absorbance, reflectance and/or emission), and the difference in the measurements (e.g., a change in absorption, reflectance and/or emission) corresponds to the amount of serum iron.

In the second phase, the pH of the mixture is increased (e.g., by adding a strongly buffered bicarbonate solution), and the components of the mixture are allowed to react (e.g., by incubating the components of the mixture). The mixture is evaluated (e.g., by measuring absorbance, reflectance and/or emission), and the difference in the measurements (e.g., a change in absorption, reflectance and/or emission) is proportional to the TIBC.

It is to be noted that using this technique, the percent iron saturation can be calculated by dividing the change in the measured parameter in the first phase by the change in the measured parameter in the second phase, multiplying by 100, and directly calibrating and reporting percent iron saturation.

The following examples are illustrative and should not be construed as limiting.

EXAMPLE I

The serum iron and TIBC of a sample were determined as follows.

A 16 microliter sample was added to 200 microliters of a reagent at time=zero seconds (see FIG. 1). The reagent contained 166 micromoles per liter of Chromazurol B, 735 micromoles per liter of Cetrimide, 16 micromoles per liter of ferric chloride, 4.1 millimoles per liter of thioure, 80.9 millimoles per liter of magnesium chloride, 0.0166% weight to volume Tween-20, and 0.002% weight to volume of ProClin 300.

These components were allowed to react for 180 seconds, and the final absorbance reading for serum iron was taken at 180 seconds. The difference between the absorbance at 180 seconds and the absorbance at zero seconds corresponds to the serum iron, which can be calculated by comparison to the absorbance of one or more calibrated samples.

60 microliters of a second reagent was then added. The second reagent contained 338 millimoles per liter of sodium bicarbonate, 772 millimoles per liter of MOPS, and 0.002% weight to volume of ProClin 300.

The final absorbance reading for TIBC was taken at 486 seconds. The difference betwen absorbance at 180 seconds and the absorbance at 486 seconds corresponds to the TIBC of the sample, which can be calculated by comparison to the absorbance of a calibrated sample.

The absorbance measurements were made using an Olympus AU400 instrument with a primary wavelength of 670 nanometers and a secondary wavelength of 340 nanometers. The instrument operated in endpoint mode. The temperature of the sample was 37° C. throughout the experiment.

EXAMPLE II

The TIBC of a sample was determined as follows.

Figure 2:
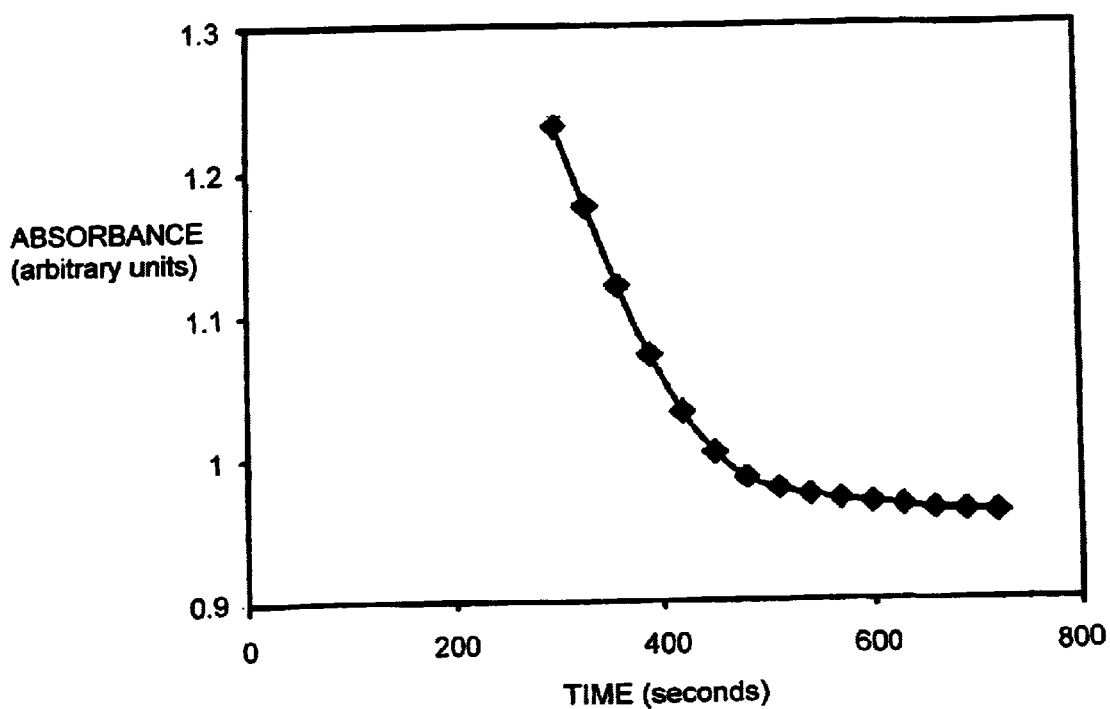
FIG. 2 is a plot of absorbance as a function of time.

A 16 microliter sample was added to 200 microliters of a reagant at time=zero seconds (see FIG. 2). The reagent contained 166 micromoles per liter of Chromazurol B, 735 micromoles per liter of Cetrimide, 16 micromoles per liter of ferric chloride, 4.1 millimoles per liter of thiourea, 80.9 millimoles per liter of magnesium chloride, 0.0166% weight to volume Tween-20, and 0.002% weight to volume of ProClin 300.

These components were allowed to react for 300 seconds.

60 microliters of a second reagent was then added. The second reagent contained 338 millimoles per liter of sodium bicarbonate, 772 millimoles per liter of MOPS, and 0.002% weight to volume of ProClin 300.

The initial absorbance reading was made at 300.5 seconds, and the final absorbance reading was taken at 720 seconds. The difference between the absorbance at 300.5 seconds and the absorbance at 720 seconds corresponds to the TIBC of the sample, which can be calculated by comparison to one or more calibrated samples.

The absorbance measurements were made using a Cobas FARA II instrument with a wavelength of 660 nanometers and. The instrument operated in endpoint mode. The temperature of the sample was 37° C. throughout the experiment.

EXAMPLE III

The TIBC of 16 samples were determined using the method described in Example II. The TIBC of the sample were also determined using the Reference Diagnostics magnetic TIBC teccnhique the results are listed in Table I.

TABLE I

| Sample | Magnetic TIBC | Direct TIBC |
| --- | --- | --- |
| 1 | 227 | 200 |
| 2 | 391 | 363 |
| 3 | 284 | 282 |
| 4 | 357 | 357 |
| 5 | 321 | 320 |
| 6 | 265 | 259 |
| 7 | 247 | 248 |

TABLE I-continued

| Sample | Magnetic TIBC | Direct TIBC |
| --- | --- | --- |
| 8 | 430 | 415 |
| 9 | 216 | 209 |
| 10 | 194 | 172 |
| 11 | 239 | 231 |
| 12 | 322 | 331 |
| 13 | 352 | 350 |
| 14 | 378 | 382 |
| 15 | 353 | 350 |
| 16 | 207 | 198 |

The mean value for the 16 samples using the magnetic TIBC method was 298.9, whereas the mean value using the method described in Example II was 291.7. The R value of the two data sets was 0.990.

While the foregoing discussion has focused on assays relating to iron, the invention is not limitet in this senses. Those skilled in the art will appreciate that the methods can also be used in assays for other analytes. For example, measurement methods (e.g., absorption measurement metheds) can be conducted using endpoint mode or by measuring the rate of change of the measured parameter (e.g., the rate of change of absorption). In some embodiments, the method can be performed more quickly by measuring the rate of change of the measured parameter. Other embodiments are in the claims.

What is claimed is:

1. A method of evaluating a sample comprising ferric ions and transferrin having binding sites for ferric ions, at least some of the binding sites of the transferrin being occupied by ferric ions, the method comprising:

providing an iron-binding dye having sites for binding to ferric ions;

combining the sample with the iron-binding dye and an excess of ferric ions to form a first mixture having a first pH so that substantially all of the ferric ions bound to the transferrin are transferred to the iron-binding dye;

making a measurement of the first mixture;

increasing the pH so that at least some of the ferric ions bound to the iron-binding dye are transferred to the transferrin, thereby forming a second mixture; and making a measurement of the second mixture.

2. The method of claim 1, wherein the iron-binding dye comprises a dye selected from the group consisting of a fluorescent dye, a colorimetric dye and combinations thereof.

3. The method of claim 1, wherein the iron-binding dye comprises a dye selected from the group consisting of Eriochromcyanine R, Chromazurol S, Chromazurol B, and combinations thereof.

4. The method of claim 1, wherein the first pH is less than about 5.7.

5. The method of claim 1, wherein the second pH is at least about 5.7.

6. The method of claim 1, wherein the method is performed in one vessel.

7. The method of claim 1, wherein the method does not include removing ferric ions from the first and second mixtures.

8. The method of claim 1, wherein the first mixture includes sufficient ferric ions so that substantially all the transferrin is saturated with ferric ions in the second mixture.

9. The method of claim 1, wherein the difference between the first and second measurements is proportional to the total iron binding capacity of the sample.

10. The method of claim 1, wherein the excess of ferric ions are combined with the iron-binding dye before being combined with the sample.

11. The method of claim 10, wherein the difference between the first and second measurements is proportional to the total iron binding capacity of the sample.

12. The method of claim 10, wherein the first pH is less than about 5.7.

13. The method of claim 10, wherein the second pH is at least about 5.7.

14. The method of claim 10, wherein the iron-binding dye comprises a dye selected from the group consisting of a fluorescent dye, a colorimetric dye and combinations thereof.

15. The method of claim 10, wherein the iron-binding dye comprises a dye selected from the group consisting of Eriochromcyanine R, Chromazurol S, Chromazurol B, and combinations thereof.

16. A method of evaluating a sample comprising ferric ions and transferrin having binding sites for ferric ions, at least some of the binding sites of the transferrin being occupied by ferric ions, the method comprising:

providing an iron-binding dye having sites for binding to ferric ions;

combining the iron-binding dye with an excess of ferric ions;

combining the sample with the iron-binding dye and the excess ferric ions to form a first mixture having a first pH so that substantially all of the ferric ions bound to the transferrin are transferred to the iron-binding dye;

making a measurement of the first mixture;

increasing the pH so that at least some of the ferric ions bound to the iron-binding dye are transferred to the transferrin, thereby forming a second mixture; and making a measurement of the second mixture, wherein the difference between the first and second measurements is proportional to the total iron binding capacity of the sample, the first pH is less than about 5.7, and the second pH is at least about 5.7.

17. The method of claim 16, wherein the iron-binding dye comprises a dye selected from the group consisting of a fluorescent dye, a colorimetric dye and combinations thereof.

18. The method of claim 16, wherein the iron-binding dye comprises a dye selected from the group consisting of Eriochromcyanine R, Chromazurol S, Chromazurol B, and combinations thereof.

19. The method of claim 16, wherein the method is performed in one vessel.

20. The method of claim 16, wherein the method does not include removing ferric ions from the first and second mixtures.

21. The method of claim 16, wherein the first mixture includes sufficient ferric ions so that substantially all the transferrin is saturated with ferric ions in the second mixture.

* * * * *